United States Patent
Guala

(10) Patent No.: US 9,919,142 B2
(45) Date of Patent: Mar. 20, 2018

(54) FLOW COMPONENT FOR MEDICAL LINES AND RELATED PRODUCTION METHOD

(71) Applicant: INDUSTRIE BORLA S.p.A., Moncalieri (Turin) (IT)

(72) Inventor: Gianni Guala, Turin (IT)

(73) Assignee: INDUSTRIE BORLA S.P.A., Moncalieri (Turin) (IT)

( * ) Notice: Subject to any disclaimer, the term of this patent is extended or adjusted under 35 U.S.C. 154(b) by 486 days.

(21) Appl. No.: 14/526,180

(22) Filed: Oct. 28, 2014

(65) Prior Publication Data

US 2015/0119819 A1   Apr. 30, 2015

(30) Foreign Application Priority Data

Oct. 28, 2013 (IT) .............................. TO2013A0868

(51) Int. Cl.
*A61M 39/06* (2006.01)
*A61M 39/04* (2006.01)
(Continued)

(52) U.S. Cl.
CPC ............ *A61M 39/06* (2013.01); *A61M 39/04* (2013.01); *A61M 39/10* (2013.01); *B29C 45/14311* (2013.01); *B29C 45/14344* (2013.01); *B29C 45/14622* (2013.01); *A61M 39/1011* (2013.01); *A61M 39/221* (2013.01); *A61M 2039/0036* (2013.01); *A61M 2039/0063* (2013.01); *A61M 2039/0205* (2013.01); *A61M 2039/0633* (2013.01); *A61M 2039/1072* (2013.01);
(Continued)

(58) Field of Classification Search
CPC ......... B29C 45/14311; B29C 45/14344; B29C 2045/1436; B29C 2045/1468; A61M 39/04; A61M 39/10; A61M 2039/0063; A61M 2039/0633; A61M 39/221; A61M 39/1011; A61M 2207/00
See application file for complete search history.

(56) References Cited

U.S. PATENT DOCUMENTS 4,552,384 A   11/1985 Cyriax
4,842,540 A   6/1989 Endo et al.
(Continued)

FOREIGN PATENT DOCUMENTS

DE   102005015343 A1   10/2006
EP   1717161 A1        11/2006
EP   1857252 A2        11/2007

OTHER PUBLICATIONS

Italian Search Report, dated Jun. 30, 2014, for corresponding Italian Patent Application No. IT 2013A000868, filed Oct. 28, 2013.

*Primary Examiner* — Bhisma Mehta
*Assistant Examiner* — Hamza Darb
(74) *Attorney, Agent, or Firm* — Heslin Rothenberg Farley & Mesiti P.C.; Victor A. Cardona, Esq.

(57) ABSTRACT

An injection site for medical lines includes a tubular body made of molded plastic material within which an elastic element made of thermoplastic material is overmolded on an enlarged end of the tubular body. The enlarged end delimits an inner annular flange and is formed with at least one radial through-hole through which the elastic element is overmolded in order to rest axially against the inner annular flange and fill the radial through-hole with an appendage.

3 Claims, 1 Drawing Sheet

(51) Int. Cl.
*A61M 39/10* (2006.01)
*B29C 45/14* (2006.01)
*B29L 31/00* (2006.01)
*A61M 39/22* (2006.01)
*A61M 39/00* (2006.01)
*A61M 39/02* (2006.01)
*B29K 101/12* (2006.01)
*B29C 45/16* (2006.01)

(52) U.S. Cl.
CPC .......... *A61M 2207/00* (2013.01); *B29C 45/16* (2013.01); *B29C 2045/14327* (2013.01); *B29C 2045/14368* (2013.01); *B29K 2101/12* (2013.01); *B29L 2031/753* (2013.01)

(56) References Cited

U.S. PATENT DOCUMENTS

| | | | |
|---|---|---|---|
| 5,611,576 A | 3/1997 | Guala | |
| 2004/0006330 A1* | 1/2004 | Fangrow, Jr. | A61M 39/02 604/533 |
| 2008/0009809 A1* | 1/2008 | Guala | A61J 1/1406 604/246 |
| 2008/0287920 A1* | 11/2008 | Fangrow | A61M 39/1011 604/535 |
| 2009/0188575 A1* | 7/2009 | Williams | F16L 37/0985 137/798 |

* cited by examiner

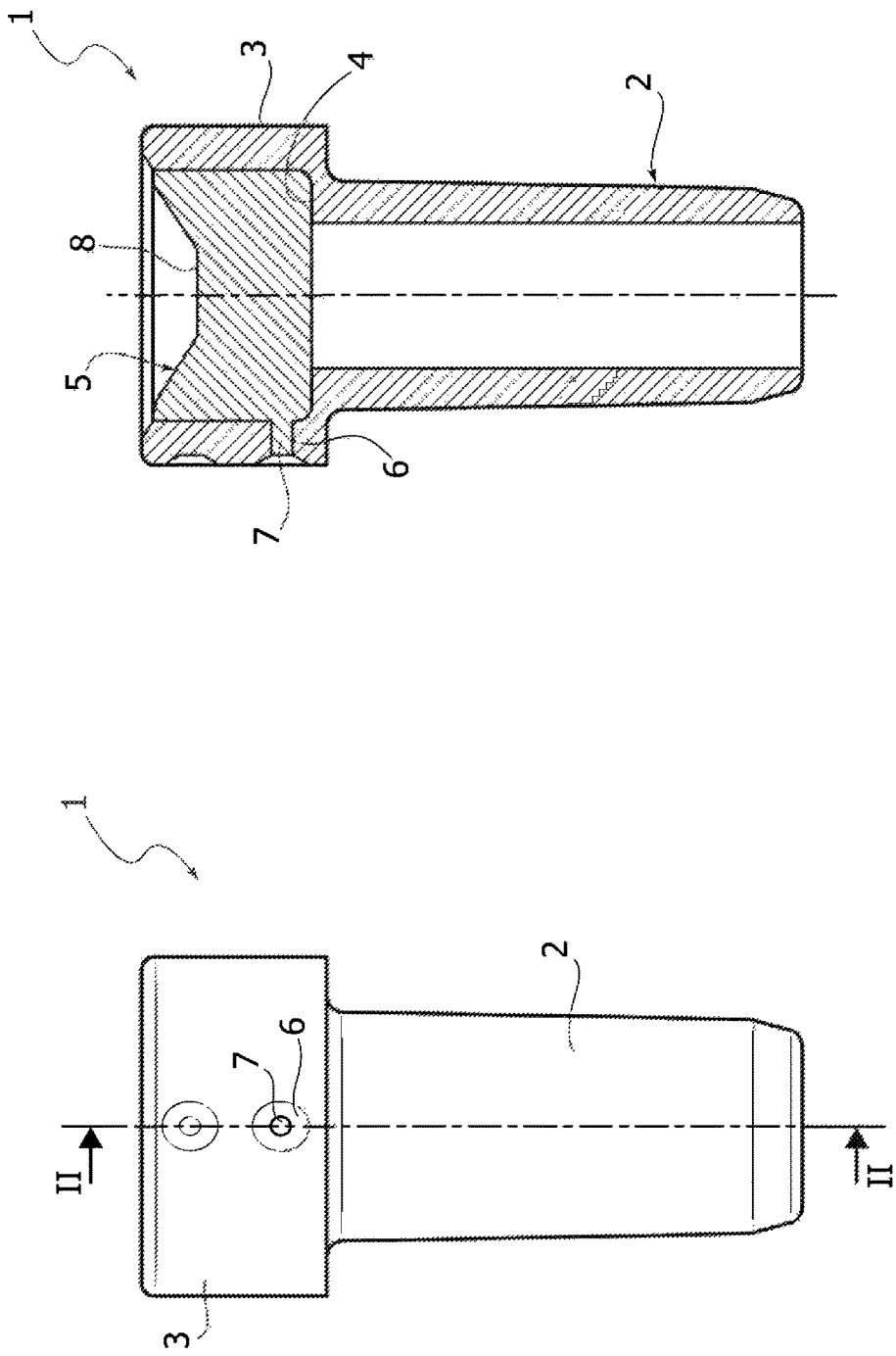

FLOW COMPONENT FOR MEDICAL LINES AND RELATED PRODUCTION METHOD

CROSS-REFERENCE TO RELATED APPLICATIONS

This application claims priority from Italian Patent Application No. TO2013A000868 filed on Oct. 28, 2013, the entire disclosure of which is incorporated herein by reference.

FIELD OF THE INVENTION

The present invention relates, in general, to flow components for medical lines including a tubular body made of molded plastic material within which a sealing element of elastic material is fitted.

In particular, the invention regards an injection site in which the element of elastic material sealingly closes one end of the tubular body and, during use, is pierceable by the introduction of a needle or cannula for administrating a medical liquid, and is then elastically reclosable following extraction of the needle or cannula.

STATE OF THE PRIOR ART

In known flow components of the type indicated above the elastic element is consisting of a relatively soft insert, formed separately and then fitted into the tubular body and fixed thereto by welding, gluing, plastic deformation of a part of the tubular body and analogous systems.

It has also been proposed, in the case of the injection site described and illustrated in document EP-1717161B1 in the name of the same Applicant, to produce the elastic element with a thermoplastic material and to overmold it within the end of the tubular body and also partly outside thereof, in order to also produce a mechanical anchoring. This solution, despite being efficient, involves certain problems: the mechanical retention of the elastic element, provided by its portion molded outside the tubular body, implicates an additional amount of the injected thermoplastic material, with the relative cost, as well as the use of relatively complicated and expensive molding equipment.

From documents US-2009/188575 DE-102005015343, U.S. Pat. No. 4,842,540 and U.S. Pat. No. 4,552,384 flow components for medical lines are known in which the elastic element, also of thermoplastic material produced by means of overmolding, is injected against the inner surface of the tubular body through at least one radial through-hole formed in the wall of the tubular body itself and within which an appendage of the elastic element remains. In all these known solutions, the elastic element is annular shaped with a thin wall and the flow components produced in this way therefore consist of tubular connectors and not of injection sites.

Document EP-1857252A2 describes an injection site corresponding to the preamble of claim 1, wherein the element of elastic material, also made of thermoplastic material and produced by overmolding or co-injection, seals one end of the tubular body and is booked to an annular axial anchoring part formed within the tubular body. This mechanical anchoring is deemed necessary to prevent, during use, displacement of the elastic element due to the axial forces applied to it during the introduction and extraction of the needle or cannula. The use of the solutions described previously, relative to thin elastic annular-shaped elements, and formed with appendages contained in the radial holes of the tubular body, is not at all considered in this document, arguably because of the conviction, perhaps even due to a technical prejudice, according to which such appendages would not be able to stably block the element of elastic material when it is subjected to the action of axial thrust or pull of the needle or cannula. The presence of the inner anchoring part involves both an obvious constructive complication of the tubular body, and difficulties associated with the subsequent overmolding of the elastic element.

SUMMARY OF THE INVENTION

The present invention aims to resolve the aforesaid drawbacks, making an injection site available for medical lines of the type defined above, producible in a simple and economic manner, without the need to form complicated mechanical anchorings within the tubular body for retaining the elastic element.

According to the invention this object is achieved thanks to the fact that the end of the tubular body is enlarged in order to delimit an inner annular flange and is formed close to this inner annular flange, with at least one radial injection through-hole, through which the elastic element is overmolded, and to the fact that the elastic element rests axially against said inner annular flange of the tubular body and has at least one appendage that fills said at least one radial through-hole.

Thanks to this solution idea, with the aid of relatively simple and economic equipment a safe anchoring of the elastic element to the tubular body is obtained, both by physical and chemical adhesion and by means of the retention provided by the inner annular flange and the radial through-hole of the tubular body. In this way the elastic element is efficiently locked both in connection with axial translation when, during use the needle or cannula is introduced and extracted through it, and also in rotation.

The invention is also directed to a method for producing the injection site, characterized in that it comprises the following steps:

producing the tubular body with one enlarged end that delimits an inner annular flange and which has, on its side wall, at least one radial injection through-hole, adjacent to said inner annular flange, injecting the thermoplastic material through said at least one radial through-hole within said enlarged end of the tubular body in such a way that the elastic element thus overmolded is blocked by means of said inner annular flange and at least one appendage that fills the or the respective radial through-hole of the tubular body.

BRIEF DESCRIPTION OF THE DRAWINGS

The invention will now be described in detail with reference to the accompanying drawings, provided purely by way of non-limiting example, in which:

FIG. 1 is a schematic elevation view of an injection site produced in accordance with the invention, and FIG. 2 is a view in axial cross-section according to the line II-II of FIG. 1.

DETAILED DESCRIPTION OF THE INVENTION

Referring to the drawings, numeral 1 indicates, in its entirety, an injection site or needle point for medical lines, including a tubular body of molded plastic material 2 having one enlarged end 3 which delimits an inner annular flange 4.

The enlarged end 3 of the tubular body 2 is filled by an elastic element 5 of a relatively soft thermoplastic material which seals the passage through the tubular body 2 and is intended to be perforated by a needle or a cannula for administrating a medicinal product to the line which, during use, is connected to the other end of the tubular body 2.

The elastic element 5 is produced by means of overmolding, injecting the thermoplastic material within the enlarged end 3 of the tubular body 2 through one or more radial injection through-holes 6 formed in the side wall of the enlarged end 3, close to the inner annular flange 4. Following the overmolding, the elastic element 5 formed as such, adheres against the side wall of the enlarged end 3 and against the inner annular flange 4, and presents an appendage 7 that remains within the radial through-hole 6, filling it. In this way, the elastic element 5 is firmly locked axially with respect to the tubular body 2, due not only to physical-chemical adhesion, but also by the inner annular flange 4 and by the radial appendage 7, which also produces the retention in rotation. This appendage 7 is completely suitable for preventing axial displacement of the elastic element 5 in the direction opposite to the inner annular flange 4 when, during use, the needle or cannula previously inserted through the elastic element 5 is extracted. Also, elastic element 5 may be located entirely radially and axially within enlarged end 3.

The elastic element 5 can be formed, in the manner shown in the example, with a recess 8 provided on the side opposite to the annular flange 4.

Of course, the details of construction and the embodiments may be widely varied with respect to those described and illustrated, without thereby departing from the scope of the present invention as defined in the following claims. Thus, for injection of the overmolding thermoplastic material of the elastic element 5, additional angularly-distributed radial holes 6 can be provided, even offset axially as well, in order to produce an even stronger mechanical retention of the elastic element 5.

The invention claimed is:

1. An injection site for medical lines including:
    a tubular body made of molded plastic material within which an elastic element is fitted which sealingly closes one end of said tubular body, wherein said elastic element is made of a thermoplastic material and is overmolded within the tubular body;
    said end of the tubular body enlarged so as to delimit an inner annular flange and at least one radial injection through-hole through which the elastic element is overmolded formed in a wall of said enlarged end close to said inner annular flange; and
    said elastic element resting axially against said inner annular flange of the enlarged end of the tubular body and having at least one appendage that fills said at least one radial through-hole;
    said elastic element configured to be pierced by a needle to allow an opening in the elastic element and provide a flow of fluid through the elastic element, said elastic element elastically closing after removal of the needle from the elastic element;
    said elastic element extending across an entire diameter of said enlarged end to sealingly close said enlarged end.

2. The injection site of claim 1 wherein said elastic element is located entirely radially and axially within said enlarged end.

3. A method for producing an injection site for medical lines including a tubular body of molded plastic material within which an elastic element is fitted, which sealingly closes said tubular body, wherein the elastic element is made of a thermoplastic material and is overmolded within the tubular body, the method comprising:
    producing the tubular body with one enlarged end that delimits an inner annular flange and which has, on a side wall of the tubular body, at least one radial injection through-hole adjacent to said inner annular flange;
    the elastic element received in the tubular body via an overmolding of the elastic element through said at least one radial injection through-hole adjacent to the inner annular flange on a side wall of the tubular body in such a way that said elastic element is blocked by means of said inner annular flange and at least one appendage filling the at least one radial through-hole of the tubular body; and
    said elastic element configured to be pierced by a needle to allow an opening in the elastic element and provide a flow of fluid through the elastic element, said elastic element elastically closing after removal of the needle from the elastic element.

* * * * *